US008048022B2

(12) United States Patent
Moy et al.

(10) Patent No.: US 8,048,022 B2
(45) Date of Patent: Nov. 1, 2011

(54) CASSETTE FOR DIFFERENTIAL PRESSURE BASED MEDICATION DELIVERY FLOW SENSOR ASSEMBLY FOR MEDICATION DELIVERY MONITORING AND METHOD OF MAKING THE SAME

(75) Inventors: Yei Feng Moy, Buffalo Grove, IL (US); John S. Ziegler, Arlington Heights, IL (US); John J. Hahn, Hartfort, WI (US); Michael G. Lowery, Wildwood, IL (US); Thomas D. Johnson, Gurnee, IL (US); James D. Jacobson, Lindenhurst, IL (US); Marwan A. Fathallah, Mundelein, IL (US)

(73) Assignee: Hospira, Inc., Lake Forest, IL (US)

( * ) Notice: Subject to any disclaimer, the term of this patent is extended or adjusted under 35 U.S.C. 154(b) by 0 days.

(21) Appl. No.: 12/469,472

(22) Filed: May 20, 2009

(65) Prior Publication Data

US 2010/0198155 A1   Aug. 5, 2010

Related U.S. Application Data

(60) Provisional application No. 61/148,786, filed on Jan. 30, 2009.

(51) Int. Cl.
| | |
|---|---|
| A61M 31/00 | (2006.01) |
| B28B 11/18 | (2006.01) |
| B29C 39/14 | (2006.01) |
| B29C 41/24 | (2006.01) |
| B29C 43/22 | (2006.01) |
| B29D 7/00 | (2006.01) |

(52) U.S. Cl. .......................................... 604/65; 264/166

(58) Field of Classification Search .................. None
See application file for complete search history.

(56) References Cited

U.S. PATENT DOCUMENTS

| 4,195,515 A | * | 4/1980 | Smoll .................. 73/861.13 |
| 4,240,294 A | * | 12/1980 | Grande ................ 73/861.47 |
| 4,261,356 A | | 4/1981 | Turner et al. |
| 4,343,316 A | | 8/1982 | Jespersen |
| 4,626,244 A | * | 12/1986 | Reinicke ................... 604/141 |

(Continued)

FOREIGN PATENT DOCUMENTS

JP         10239193 A         9/1998

(Continued)

OTHER PUBLICATIONS

Alan F. Merry, Craig S. Webster and Daniel J. Matthew et al. A New Safety-Oriented Integrated Drug Administration and Automated Anesthesia Record System. Anesth Analg 2001;93:385-90.

(Continued)

*Primary Examiner* — Nicholas Lucchesi
*Assistant Examiner* — Pritesh Patel
(74) *Attorney, Agent, or Firm* — Michael R. Crabb

(57) ABSTRACT

A disposable assembly for use with a sensor assembly, the disposable comprising a body, a flow restricting element, and a fluid pressure membrane. The body has a lid portion and a base portion. The body defines a fluid flow passage that forms an inlet and an outlet. The flow restricting element is positioned in the fluid flow passage between the inlet and the outlet. The fluid pressure membrane is disposed along the fluid flow passage between the inlet and the outlet. The fluid pressure membrane is located between the lid portion and the base portion of the body.

15 Claims, 13 Drawing Sheets

U.S. PATENT DOCUMENTS

| | | | |
|---|---|---|---|
| 4,694,273 A * | 9/1987 | Franchino | 340/447 |
| 4,758,228 A | 7/1988 | Williams | |
| 4,856,339 A | 8/1989 | Williams | |
| 4,881,413 A | 11/1989 | Georgi et al. | |
| 4,892,656 A * | 1/1990 | Pietzsch | 210/232 |
| 4,938,079 A | 7/1990 | Goldberg | |
| 4,947,856 A | 8/1990 | Beard | |
| 5,211,626 A | 5/1993 | Frank et al. | |
| 5,242,406 A | 9/1993 | Gross et al. | |
| 5,287,851 A | 2/1994 | Beran et al. | |
| 5,292,306 A | 3/1994 | Wynkoop et al. | |
| 5,325,728 A | 7/1994 | Zimmerman et al. | |
| 5,417,119 A | 5/1995 | Smoll | |
| 5,417,395 A | 5/1995 | Fowler et al. | |
| 5,450,758 A | 9/1995 | Smoll | |
| 5,463,906 A | 11/1995 | Spani et al. | |
| 5,611,784 A | 3/1997 | Barresi et al. | |
| 5,628,309 A | 5/1997 | Brown | |
| 5,651,775 A | 7/1997 | Walker et al. | |
| 5,672,832 A | 9/1997 | Cucci et al. | |
| 5,697,916 A | 12/1997 | Schraga | |
| 5,728,074 A | 3/1998 | Castellano et al. | |
| 5,752,918 A | 5/1998 | Fowler et al. | |
| 5,758,643 A | 6/1998 | Wong et al. | |
| 5,805,455 A | 9/1998 | Lipps | |
| 5,848,971 A | 12/1998 | Fowler et al. | |
| 5,891,051 A | 4/1999 | Han et al. | |
| 5,904,666 A | 5/1999 | DeDecker et al. | |
| 5,944,660 A | 8/1999 | Kimball et al. | |
| 5,947,911 A | 9/1999 | Wong et al. | |
| 6,032,536 A * | 3/2000 | Peeters et al. | 73/725 |
| 6,068,615 A | 5/2000 | Brown et al. | |
| 6,250,132 B1 | 6/2001 | Drzewiecki | |
| 6,270,455 B1 | 8/2001 | Brown | |
| 6,272,934 B1 | 8/2001 | Rajan et al. | |
| 6,277,099 B1 | 8/2001 | Strowe et al. | |
| 6,349,740 B1 | 2/2002 | Cho et al. | |
| 6,385,505 B1 | 5/2002 | Lipps | |
| 6,386,050 B1 | 5/2002 | Yin et al. | |
| 6,445,053 B1 | 9/2002 | Cho | |
| 6,482,185 B1 | 11/2002 | Hartmann | |
| 6,558,125 B1 | 5/2003 | Futterknecht | |
| 6,578,435 B2 | 6/2003 | Gould et al. | |
| RE38,189 E | 7/2003 | Walker et al. | |
| 6,609,047 B1 | 8/2003 | Lipps | |
| D481,121 S | 10/2003 | Evans | |
| D485,356 S | 1/2004 | Evans | |
| 6,685,668 B1 | 2/2004 | Cho et al. | |
| 6,685,678 B2 | 2/2004 | Evans et al. | |
| 6,700,174 B1 | 3/2004 | Miu et al. | |
| 6,700,784 B2 * | 3/2004 | Huang et al. | 361/715 |
| 6,760,643 B2 | 7/2004 | Lipps | |
| 6,813,964 B1 | 11/2004 | Clark et al. | |
| 6,920,795 B2 | 7/2005 | Bischoff et al. | |
| 6,932,796 B2 | 8/2005 | Sage et al. | |
| 6,935,192 B2 | 8/2005 | Sobek et al. | |
| 6,964,204 B2 | 11/2005 | Clark et al. | |
| 6,975,922 B2 | 12/2005 | Duncan et al. | |
| 6,981,960 B2 | 1/2006 | Cho et al. | |
| 7,059,184 B2 | 6/2006 | Kanouola et al. | |
| 7,074,209 B2 | 7/2006 | Evans et al. | |
| 7,082,843 B2 | 8/2006 | Clark et al. | |
| 7,096,729 B2 | 8/2006 | Repko et al. | |
| 7,115,113 B2 | 10/2006 | Evans et al. | |
| 7,161,488 B2 | 1/2007 | Frasch | |
| 7,162,290 B1 | 1/2007 | Levin | |
| 7,162,927 B1 | 1/2007 | Selvan et al. | |
| 7,415,895 B2 | 8/2008 | Kurisaki et al. | |
| 7,503,903 B2 | 3/2009 | Carlisle et al. | |
| 7,571,024 B2 | 8/2009 | Duncan et al. | |
| 7,693,697 B2 | 4/2010 | Westenkow et al. | |
| 7,775,126 B2 | 8/2010 | Eckhardt et al. | |
| 7,775,127 B2 | 8/2010 | Wade | |
| 7,819,838 B2 * | 10/2010 | Ziegler et al. | 604/65 |
| 2002/0099334 A1 | 7/2002 | Hanson et al. | |
| 2002/0123741 A1 | 9/2002 | Rake et al. | |
| 2003/0065537 A1 | 4/2003 | Evans | |
| 2004/0082918 A1 | 4/2004 | Evans et al. | |
| 2004/0225409 A1 | 11/2004 | Duncan et al. | |
| 2004/0232219 A1 | 11/2004 | Fowler | |
| 2004/0251406 A1 * | 12/2004 | Figueria | 250/231.1 |
| 2006/0142692 A1 | 6/2006 | Jacobson et al. | |
| 2006/0181695 A1 | 8/2006 | Sage, Jr. | |
| 2006/0260416 A1 | 11/2006 | Sage et al. | |
| 2006/0266128 A1 * | 11/2006 | Clark et al. | 73/861.52 |
| 2007/0060872 A1 | 3/2007 | Hall et al. | |
| 2007/0129618 A1 | 6/2007 | Goldberger et al. | |
| 2007/0179436 A1 | 8/2007 | Braig et al. | |
| 2009/0004767 A1 * | 1/2009 | Parks et al. | 438/53 |
| 2009/0157040 A1 | 6/2009 | Jacobson et al. | |
| 2009/0288497 A1 | 11/2009 | Ziegler et al. | |

FOREIGN PATENT DOCUMENTS

| | | |
|---|---|---|
| JP | 2007071695 | 3/2007 |
| WO | 0227276 A2 | 4/2002 |
| WO | 2005082450 A1 | 9/2005 |
| WO | 2005118015 A1 | 12/2005 |

OTHER PUBLICATIONS

Dec. 2005 Advertisement from SensorONE Ltd for the Series PD-39 X Differential Pressure Transmitter.
2005 Advertisement form BARD for the CritiCore Monitor.

* cited by examiner

US 8,048,022 B2

CASSETTE FOR DIFFERENTIAL PRESSURE BASED MEDICATION DELIVERY FLOW SENSOR ASSEMBLY FOR MEDICATION DELIVERY MONITORING AND METHOD OF MAKING THE SAME

CROSS REFERENCE TO RELATED APPLICATIONS

This application claims priority under 35 U.S.C. 119 of U.S. Ser. No. 61/148,786 filed Jan. 30, 2009.

TECHNICAL FIELD

The present invention generally relates to a differential pressure based flow sensor assembly and method for monitoring medication delivery utilizing a system containing the differential pressure based flow sensor assembly, and more particularly to a differential pressure based flow sensor assembly that has a disposable portion and a reusable portion. More particularly, the present invention relates to a cassette to serve as the disposable portion of such a flow sensor assembly that is economical to produce and easy to assemble.

BACKGROUND

Modern medical devices, including medical pumps, are increasingly being controlled by microprocessor based systems to deliver fluids, solutions, medications, and drugs to patients. A typical control for a medical pump includes a user interface enabling a medical practitioner to enter the dosage of fluid to be delivered, the rate of fluid delivery, the duration, and the volume of a fluid to be infused into a patient. Typically, drug delivery is programmed to occur as a continuous infusion or as a single bolus dose.

It is common for a plurality of medications to be infused to a patient by using a multi-channel infusion pump or using a plurality of single channel infusion pumps where a different fluid is administered from each channel. Another method of delivering multiple medications to a patient is to deliver a first medication using an infusion pump, and additional medications through single bolus doses.

When delivering medications through single bolus doses it is important to verify that correct medications are being delivered to the patient as well as to verify that the correct amount of medication is being delivered to the patient. Typically a caregiver simply manually notes on the patient's paper chart the amount of medication delivered via a bolus dose, and that information may later be entered into a patient's record electronically. Thus, human error may lead to an accidental overdose or underdose of a medication, while a caregiver believes that a proper dose was delivered. In addition to an error in medication dosing, it is also possible that human error may result in the failure to record the medication delivered during a single bolus dose. Thus, it is possible that a patient's medical records may not reflect every medication that patient has been given. A sensor within the IV line capable of measuring a wide range of fluids and flow rates would be helpful in documenting the flow rate and volume of every medication the patient is given through that line. Further, it is desirable to provide a robust flow rate sensing methodology that is low cost and in particular introduces low incremental cost to the disposable medication delivery tubing set. Further, it is desirable to provide a flow rate sensing methodology that is capable of accurately sensing the flow rate of fluids that have a range of physical properties, including fluid viscosity, which may not be known precisely. Further, any flow sensor must be manufactured accurately and affordably. Therefore, a need exists for a flow sensor system adapted for monitoring medication delivery that is also designed for more efficient manufacturing.

SUMMARY

According to one embodiment, a disposable assembly for use with a flow sensor assembly is provided. The disposable assembly comprises a body, a flow restricting element, and a fluid pressure membrane. The body has a lid portion and a base portion. The body defines a fluid flow passage that forms an inlet and an outlet. The lid portion has a first opening and a second opening. The flow restricting element is positioned along the fluid flow passage between the inlet and the outlet. The flow restricting element is formed into the base portion of the body. The fluid pressure membrane is located in the fluid flow path between the inlet and the outlet. The fluid pressure membrane is located between the lid portion and the base portion of the body.

According to another embodiment, a disposable assembly for use with a sensor assembly comprises a body, a flow restricting element, a fluid pressure membrane, a first rigid disk and a second rigid disk. The body has a lid portion and a base portion. The body defines a flow passage forming an inlet and an outlet. The flow restricting element is positioned in the fluid flow passage between the inlet and the outlet. The flow restricting element is formed within the base portion. The fluid pressure membrane is located along the fluid flow passage between the inlet and the outlet. The fluid pressure membrane is located between the lid portion and the base portion of the body. The first rigid disk is positioned between the fluid pressure membrane and the lid. The first rigid disk is positioned near a first opening formed in the lid. The second rigid disk is positioned between the fluid pressure membrane and the lid. The second rigid disk is positioned near a second opening formed in the lid.

According to one method a disposable portion for a fluid flow sensor assembly is formed. The method provides a preformed flow restricting element. A base portion forms around the flow restricting element. The base portion forms at least a portion of a fluid flow passage having an inlet and an outlet respectively disposed upstream and downstream of the flow restricting element. A fluid pressure membrane is positioned along the fluid flow passage between the inlet and the outlet. The fluid pressure membrane contacts the base portion. A lid portion is secured to the base portion. The fluid pressure membrane is positioned or captured between the lid portion and the base portion.

DETAILED DESCRIPTION

Figure 1:
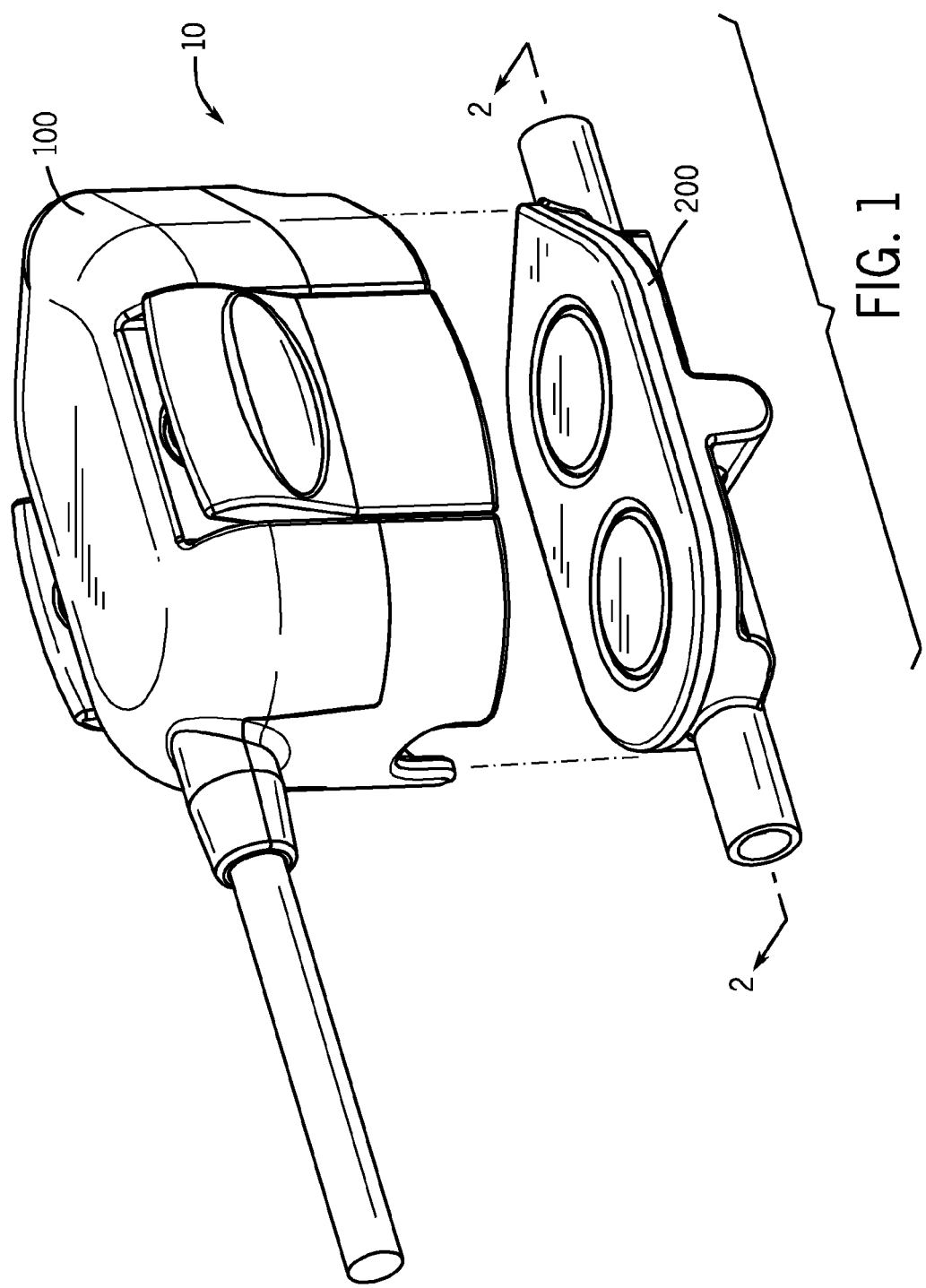
FIG. 1 is a pictorial view that illustrates a differential pressure based flow sensor assembly with a reusable portion and a disposable portion in a disassembled state according to one embodiment.

While this invention is susceptible of embodiments in many different forms, there is shown in the drawings and will herein be described an example of the invention. The present disclosure is to be considered as an example of the principles of the invention. It is not intended to limit the broad aspect of the invention to the examples illustrated.

FIG. 1 is a pictorial representation of a differential pressure based flow sensor assembly 10 in an unassembled state. The differential pressure based flow sensor assembly comprises a reusable portion 100 and a disposable portion 200. The disposable portion 200 is releasably coupled with the reusable portion 100

Figure 2:
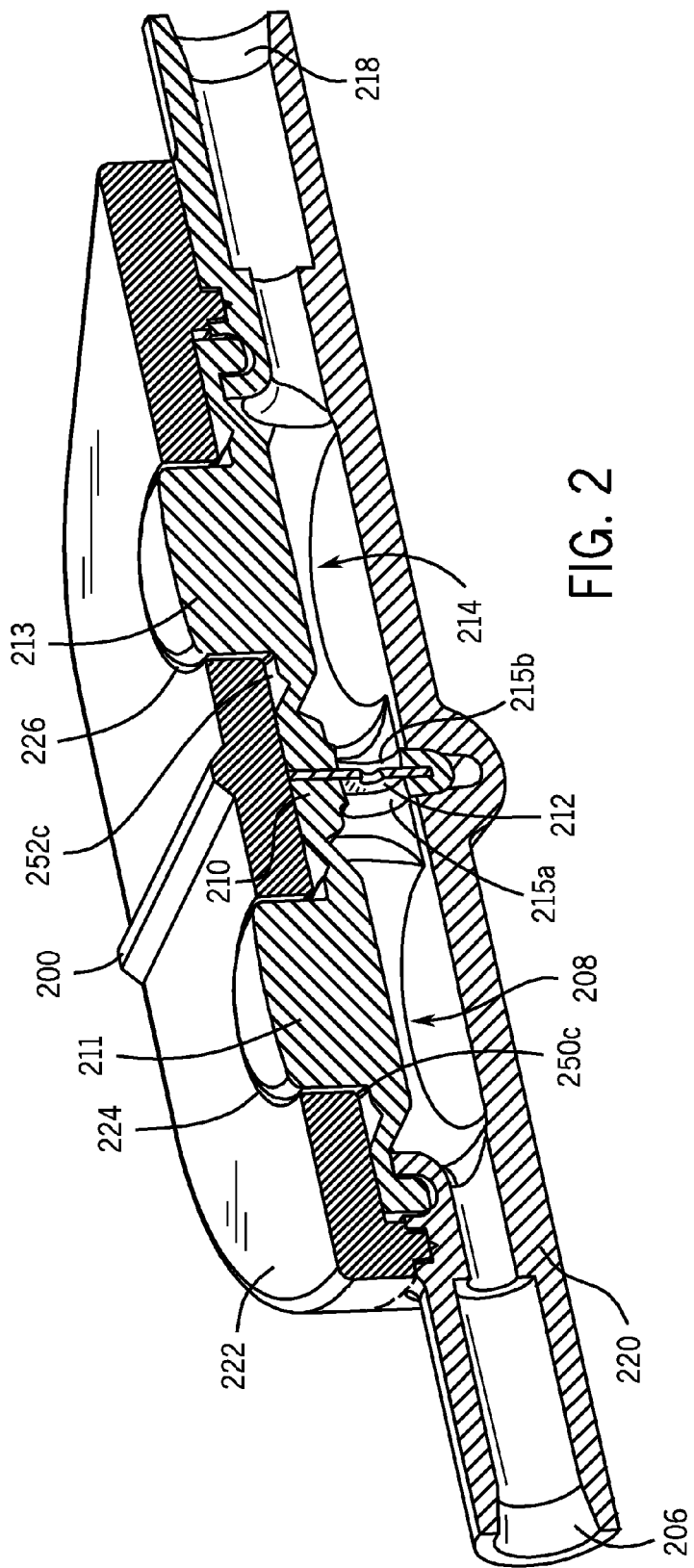
FIG. 2 shows a cross sectional view taken along line 2-2 in FIG. 1 of the disposable portion of the embodiment shown in FIG. 1.

As better shown in FIG. 2, the disposable portion 200 comprises: a fluid inlet 206; an upstream fluid chamber 208; a fluid pressure membrane 210; a flow restricting element 212 with an orifice 201 therethrough; a downstream fluid chamber 214; and a fluid outlet 218. The membrane 210 is fluid impermeable. The disposable portion 200 has a base 220 and a lid 222. the external contours or perimeters of the mating surfaces of the base 220 and lid 222 are different at different longitudinal ends (from left to right in the drawing) to ensure that the disposable portion 200 is oriented correctly in the reusable portion 100.

Figure 3:
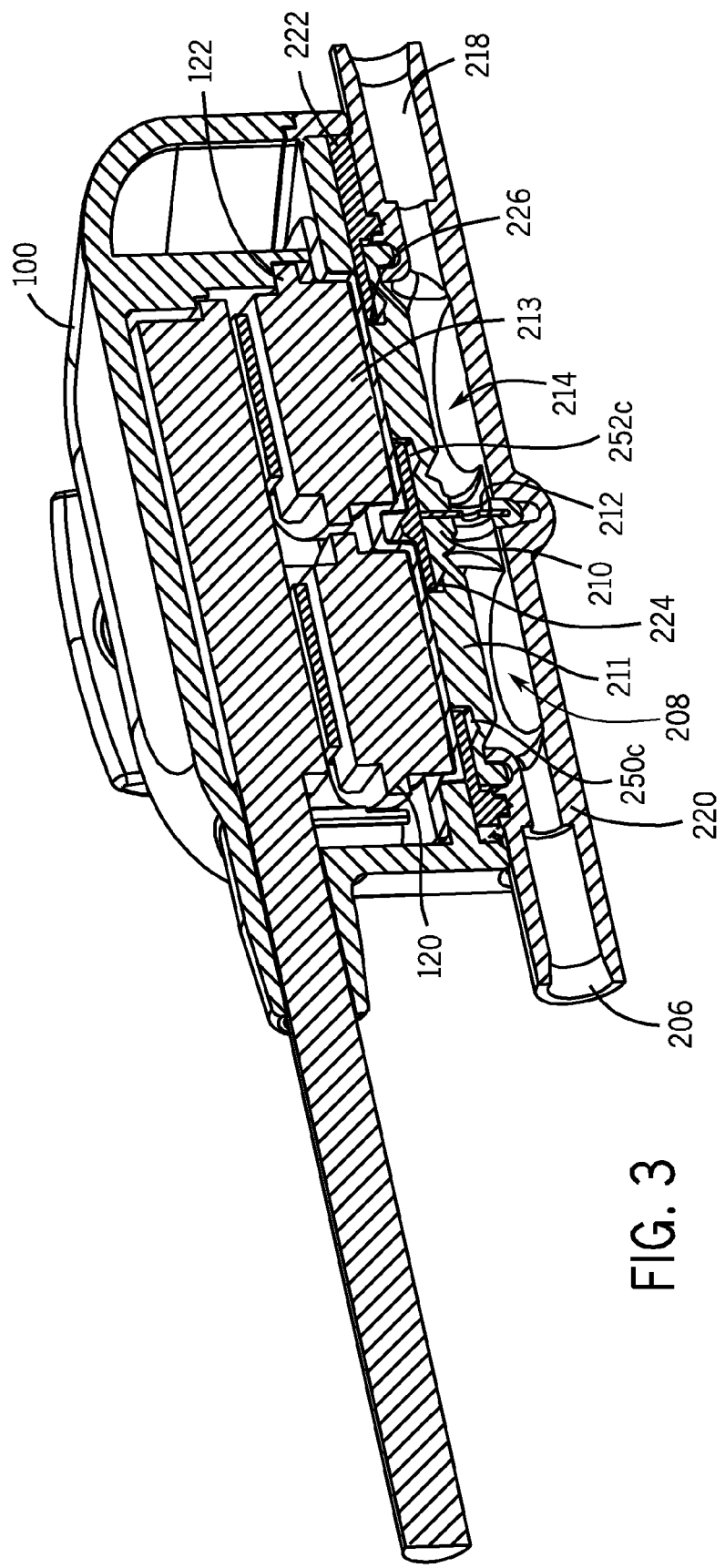
FIG. 3 is a cross sectional view of the differential pressure based flow sensor assembly of FIG. 1 in an assembled state taken along line 2-2 of FIG. 1.

As shown in FIGS. 1-3, medication, or some other fluid, enters the disposable portion 200 through the fluid inlet 206. The medication flows into the upstream fluid chamber 208 from the fluid inlet 206. Next, the medication flows through the flow restricting element 212 and into the downstream fluid chamber 214. The flow of the medication through the flow restricting element 212 results in a drop in fluid pressure as the fluid flows from the upstream fluid chamber 208 to the downstream fluid chamber 214 through the flow restricting element 212. Thus, during forward fluid flow under normal conditions, the fluid pressure within the upstream fluid chamber 208 is generally greater the fluid pressure within the downstream fluid chamber 214. The fluid pressure within the upstream fluid chamber 208 presses against a first area 211 of the fluid pressure membrane 210. Similarly, the fluid pressure within the downstream fluid chamber 214 presses against a second area 213 of the fluid pressure membrane 210.

The lid 222 forms an upstream opening 224 and a downstream opening 226 to allow the first and second areas 211, 213 of the fluid pressure membrane 210 to communicate, respectively, with the upstream pressure sensor 120 and the downstream pressure sensor 122 of the reusable portion 100. The first and second areas 211, 213 may be raised to extend into or more preferably through the openings 224, 226 to engage the sensors 120, 122. Raising the first and second areas 211, 213 additionally aids in the positioning of the lid 222 and the membrane 210 during assembly.

The lid 222 is positioned such that the fluid pressure membrane 210 is positioned between the base 220 and the lid 222. The lid 222 and the base 220 are joined together to capture the fluid pressure membrane 210 between them. The lid 222 and the base 220 may be ultrasonically welded together to form a fully assembled disposable portion 202, as viewed in FIG. 1. The fluid pressure membrane 210 may thus be firmly secured between the base 220 and the lid 222 without the use of any adhesive to fasten the fluid pressure membrane 210 to either the base 220 or the lid 222.

As shown in FIGS. 1-3, the fluid pressure membrane 210 is a flexible diaphragm type membrane. The fluid pressure membrane 210 may be formed from silicone, or some other flexible polymeric material or elastomeric material. In one embodiment, the membrane 210 has a fold therein that holds the flow restricting element 212 and includes fluid passages 215a, 215b in fluid communication with the flow restricting element 212 so that fluid may flow therethrough and between the upstream and downstream fluid chambers 208, 214. In another embodiment, the flow restricting element can be held in slots formed in the underside of the membrane 210 and the upper side of the base 220, avoiding the need for the fold and the fluid passages 215a, 215b. In FIGS. 2-3, the membrane 210 has an increased thickness at the first and second areas 211, 213 in order to raise the fluid pressure at which the membrane 210 fails. Situations where the disposable portion 200 is subjected to higher fluid pressures than expected may include: a manual bolus dose that is provided too quickly; the disposable portion 200 not being used with the reusable portion 100, as may occur when a patient is being moved; or the disposable portion 200 is not positioned properly with the reusable portion 100.

In addition to the first and second areas 211, 213 having an increased thickness, a thickened ring 250c, 252c surrounds each of the first and second areas 211, 213. The thickened rings 250c, 252c are located between the membrane 210 and the lid 222 of the disposable portion 200. Thus, as pressure is applied to the membrane 210, the first and second areas 211, 213 of the membrane 210 are pushed upward through the openings 224, 226 of the lid 222. The thickened rings 250c, 252c contact the lid 222 as the membrane 210 is raised by the pressure of the fluid flow. Once the thickened rings 250c, 252c contact the lid 222 the first and second areas 211, 213 of the membrane 210 may continue to be displaced through the opening 224, 226 of the lid. Thus, the increased thickness of the first and second areas 211, 213 provide additional strength to the membrane 210, increasing the pressure level at which the membrane 210 will fail.

The use of the thickened rings 250c, 252c allows the disposable portion 200 to withstand higher operating pressures, without causing the thickness of the membrane 210 in the areas just outside thickened rings 250c, 252c to become so thick that sensitivity of the sensor assembly 10 is degraded.

It is contemplated that a variety of materials may be utilized for the manufacture of the disposable portion 200. The disposable portion 200 may comprise a thermoplastic. It is contemplated that the flow restricting element 212 may be made of the same thermoplastic as the rest of the disposable portion 200, or may be a different material than the disposable portion 200. Non-limiting examples of the material that may be utilized to form the flow restricting element 212 include silicon, glass, and medical grade thermoplastics and elastomers. The flow restricting element 212 even can be made in whole or in part of stainless steel or other metal. A stainless steel orifice plate can be encased in a thermoplastic or elastomeric frame. The orifice 201 in the flow restricting element 212 can be formed by molding, laser microdrilling, chemical etching, die cutting or stamping. The fluid pressure membranes 210 may comprise a variety of polymeric or elastomeric materials, such as TPE, or silicone.

As shown in FIG. 3, medication enters the disposable portion 200 through the fluid inlet 206. The medication flows into the upstream fluid chamber 208 from the fluid inlet 206. Next, the medication flows through the flow restricting element 212 and into the downstream fluid chamber 214. The flow of the medication through the flow restricting element 212 results in a drop in fluid pressure as the fluid flows from the upstream fluid chamber 208 to the downstream fluid chamber 214 through the flow restricting element 212. Thus, during forward fluid flow under normal conditions, the fluid pressure within the upstream fluid chamber 208 is generally greater the fluid pressure within the downstream fluid chamber 214. The fluid pressure within the upstream fluid chamber 208 presses against the first area 211 fluid pressure membrane 210, causing the first area 211 of the membrane 210 to pass through the upstream opening 224 of the lid 222 to press against the upstream fluid pressure sensor 120. Similarly, the fluid pressure within the downstream fluid chamber 214 presses against the second area 213 of the fluid pressure membrane 210, causing the second area 213 of the membrane 210 to pass through the downstream opening 226 of the lid 222 to press against the downstream fluid pressure sensor 122.

Figure 4:
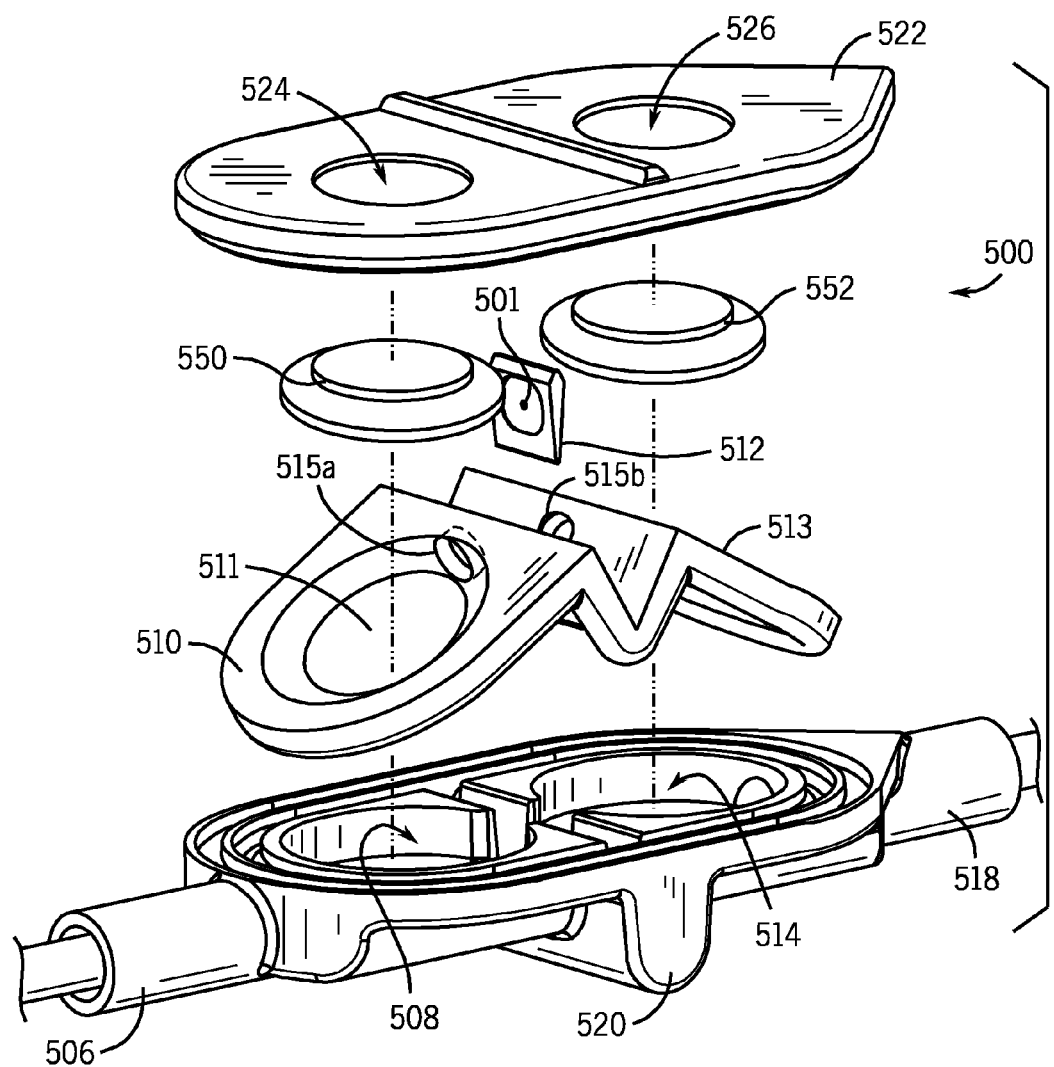
FIG. 4 is an exploded view of a disposable portion of a differential pressure based flow sensor assembly according to another embodiment.
Figure 5:
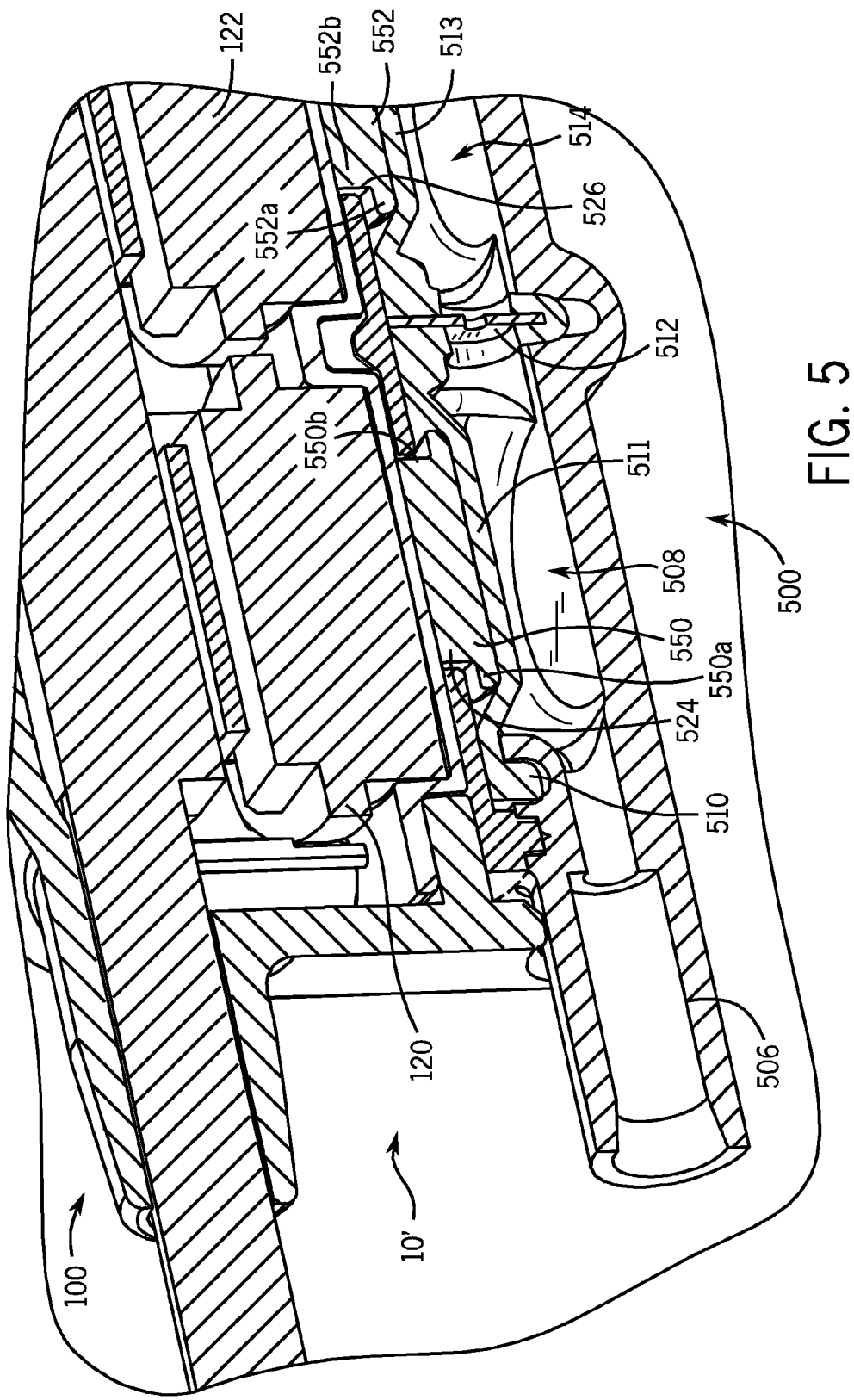
FIG. 5 is a partial cross sectional view of a differential pressure based flow sensor assembly having the disposable portion of FIG. 4.
Figure 6:
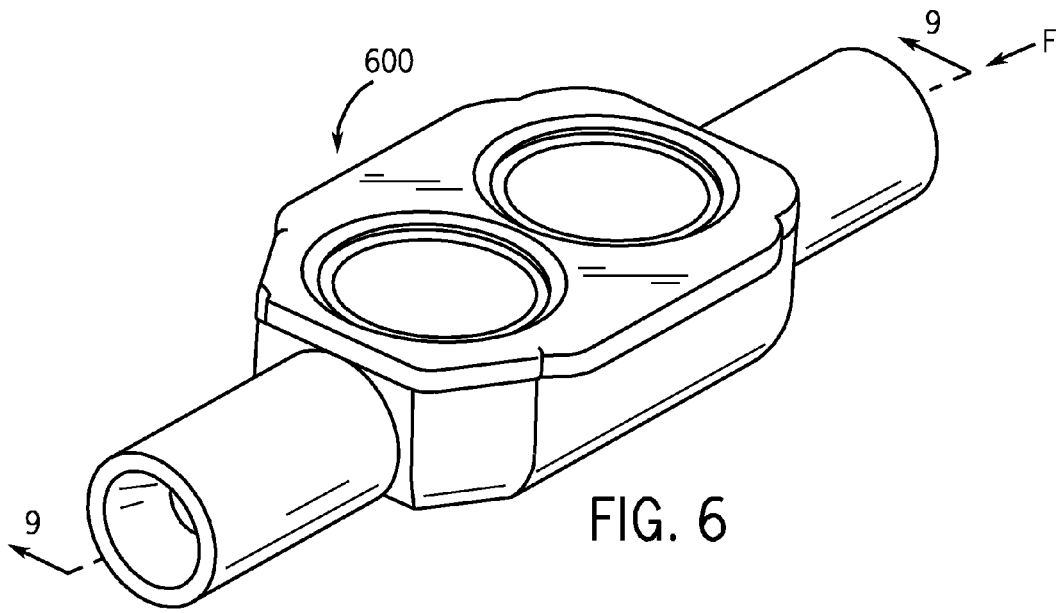
FIG. 6 is a pictorial view of a disposable portion of a differential pressure based flow sensor assembly according to a further embodiment.
Figure 7:
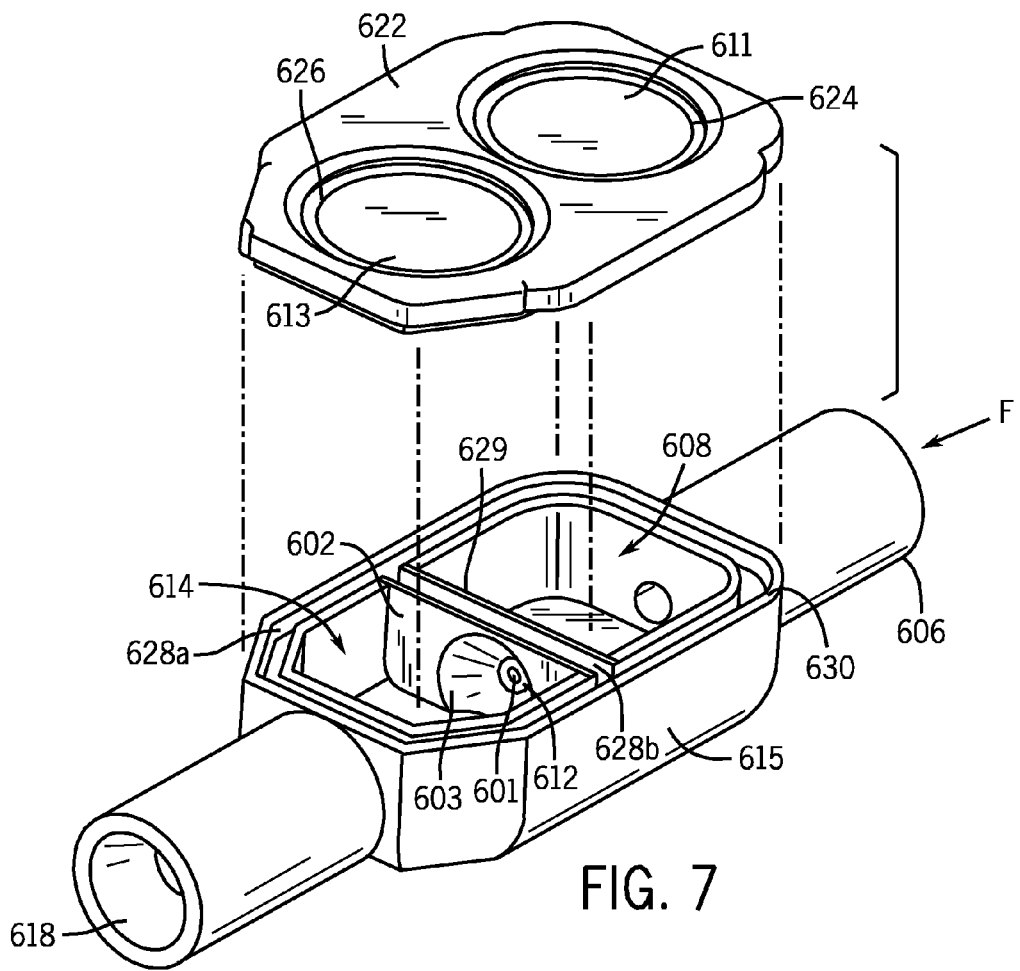
FIG. 7 is an exploded view of the disposable portion of the differential pressure based flow sensor assembly of FIG. 6.

FIG. 4 is an exploded pictorial representation of a disposable portion 500 for a differential pressure based flow sensor assembly 10' (FIG. 5). The differential pressure based flow sensor assembly 10' comprises the reusable portion 100 and the disposable portion 500.

The disposable portion 500 comprises: a fluid inlet 506; an upstream fluid chamber 508; a fluid pressure membrane 510; a flow restricting element 512 with an orifice 501 therethrough; a downstream fluid chamber 514; and a fluid outlet 518. The membrane 510 is fluid impermeable. In one embodiment, the membrane has a fold therein that holds the flow restricting element 512 and includes fluid passages 515a, 515b in fluid communication with the flow restricting element 512 so that fluid may flow therethrough and between the upstream and downstream fluid chambers 508, 514. The disposable portion 500 has a base 520 and a lid 522. The external contours of the base 520 and lid 522 are different from left to right to ensure that the disposable portion 500 is oriented correctly in the reusable portion 100. The external contours or perimeters of the mating surfaces of the base 520 and lid 522 are different at different longitudinal ends (from left to right in the drawing) to ensure that the disposable portion 500 is oriented correctly in the reusable portion 100.

As shown in FIGS. 4-5, medication, or some other fluid, enters the disposable portion 500 through the fluid inlet 506. The medication flows into the upstream fluid chamber 508 from the fluid inlet 506. Next, the medication flows through the flow restricting element 512 and into the downstream fluid chamber 514. The flow of the medication through the flow restricting element 512 results in a drop in fluid pressure as the fluid flows from the upstream fluid chamber 508 to the downstream fluid chamber 514 through the flow restricting element 512. Thus, during forward fluid flow under normal conditions, the fluid pressure within the upstream fluid chamber 508 is generally greater the fluid pressure within the downstream fluid chamber 514. The fluid pressure within the upstream fluid chamber 508 presses against a first area 511 of the fluid pressure membrane 510. Similarly, the fluid pressure within the downstream fluid chamber 514 presses against a second area 513 of the fluid pressure membrane 510.

The lid 522 forms an upstream opening 524 and a downstream opening 526 to allow the first and second areas 511, 513 of the fluid pressure membrane 510 to communicate, respectively, with the upstream pressure sensor 120 and the downstream pressure sensor 122 of the reusable portion 100.

The lid 522 is positioned such that the fluid pressure membrane 510 is positioned between the base 520 and the lid 522. The lid 522 and the base 520 are joined together to capture the fluid pressure membrane 510 between them. The lid 522 and the base 520 may be laser or ultrasonically welded together to form a fully assembled disposable portion 500, as viewed in FIG. 5. The fluid pressure membrane 510 may thus be firmly secured between the base 520 and the lid 522 without the use of any adhesive to fasten the fluid pressure membrane 510 to either the base 520 or the lid 522.

As shown in FIGS. 4-5, rigid disks 550, 552 are positioned above each of the first and second areas 51 1, 513 of the membrane 510 between the membrane 510 and the lid 522. Thus, as pressure is applied to the membrane 510, the first and second areas 511, 513 of the membrane 510 are pushed upward towards the openings 524, 526 of the lid 522, thus moving the rigid disks 550, 552 towards the openings 524, 526. The rigid disks 550, 552 contact the lid 522 as the membrane 510 is raised by the pressure of the fluid flow. Once the rigid disks 550, 552 contact the lid 522 the first and second areas 511, 513 of the membrane 510 are constrained and may not continue to move towards the lid 522. Thus, the rigid disks 550, 552 prevent the membrane 510 from being displaced to an extent that the membrane 510 is likely to fail.

The use of the rigid disks 550, 552 allows the disposable portion 500 to withstand higher operating pressures, without causing the thickness of the membrane 510 in the first and second areas 511, 513 to be different than the rest of the membrane 510.

The rigid disk 550 has a ledge portion 550a that is adapted to contact the lid 522, and a protruding portion 550b that is adapted to interact with a sensor 120 within the reusable portion 100. Thus, as fluid flows through the disposable portion 500, the first area 511 of the membrane 510 is displaced toward the lid 522, causing the protruding portion 550b of the rigid disk 550 to pass through the opening 524 of the lid 522. However, once the pressure within the upstream chamber 508 reaches a certain level, the ledge portion 550a of the rigid disk 550 contacts the lid 522, preventing further displacement of the first area 511 of the membrane 510.

Similarly, the rigid disk 552 has a ledge portion 552a that is adapted to contact the lid 522, and a protruding portion 552b that is adapted to interact with a sensor 122 within the reusable portion 100. Thus, as fluid flows through the disposable portion 500, the second area 513 of the membrane 510 is displaced toward the lid 522, causing the protruding portion 552b of the rigid disk 550 to pass through the opening 526 of the lid 522. However, once the pressure within the downstream chamber 514 reaches a certain level, the ledge portion 552a of the rigid disk 552 contacts the lid 522, preventing further displacement of the second area 513 of the membrane 510.

Therefore, the membrane 510 may be subjected to much higher pressure before failing based on the rigid disks 550, 552 limiting the displacement of the membrane 510.

As shown in FIGS. 4-5, the fluid pressure membrane 510 is a flexible diaphragm type membrane. The fluid pressure membrane 510 may be formed from silicone, or some other flexible polymeric material or elastomeric material. In FIGS. 4-5, the membrane 510 may have a depression formed at the first and second areas 511, 513 in order to allow the rigid disks 550, 552 to be positioned between the membrane 510 and the lid 522.

It is contemplated that a variety of materials may be utilized for the manufacture of the disposable portion 500. The disposable portion 500 may comprise a thermoplastic. It is contemplated that the flow restricting element 512 may be made of the same thermoplastic as the rest of the disposable portion 500, or may be a different material than the disposable portion 500. Non-limiting examples of the material that may be utilized to form the flow restricting element 512 include silicon, glass, and medical grade thermoplastics and elastomers. The flow restricting element 512 even can be made in whole or in part of stainless steel or other metal. A stainless steel orifice plate can be encased in a thermoplastic or elastomeric frame. The orifice 501 in the flow restricting element 512 can be formed by molding, laser microdrilling, chemical etching, die cutting or stamping. The fluid pressure membrane 510 may comprise a variety of polymeric or elastomeric materials, such as TPE, or silicone.

As shown in FIG. 5, medication enters the disposable portion 500 through the fluid inlet 506. The medication flows into the upstream fluid chamber 508 from the fluid inlet 506. Next, the medication flows through the flow restricting element 512 and into the downstream fluid chamber 514. The flow of the medication through the flow restricting element 512 results in a drop in fluid pressure as the fluid flows from the upstream fluid chamber 508 to the downstream fluid chamber 514 through the flow restricting element 512. Thus, during forward fluid flow under normal conditions, the fluid pressure within the upstream fluid chamber 508 is generally greater the fluid pressure within the downstream fluid chamber 514. The fluid pressure within the upstream fluid chamber 508 presses against the first area 511 fluid pressure membrane 510, causing the first area 511 of the membrane 510 to press against the rigid disk 550 and cause the protruding portion 550b of the disk 550 to pass through the upstream opening 524 of the lid 522 to press against the upstream fluid pressure sensor 120.

Similarly, the fluid pressure within the downstream fluid chamber 514 presses against the second area 513 of the fluid pressure membrane 510, causing the second area 513 of the membrane 510 to press against the rigid disk 552 and cause the protruding portion 552b of the disk 552 to pass through the downstream opening 526 of the lid 522 to press against the downstream fluid pressure sensor 122.

Turning next to FIGS. 6-9 a disposable portion 600 according to a further embodiment is shown. The disposable portion 600 has been rotated end for end to make certain features easier to see. The normal fluid flow F is from right to left, which is opposite that shown in FIGS. 1-5. The disposable portion 600 comprises: a fluid inlet 606; an upstream fluid chamber 608; a fluid pressure membrane 610; a flow restricting element 612 with orifice 601 formed therethrough; a downstream fluid chamber 614; and a fluid outlet 618. The membrane 610 is fluid impermeable. The disposable portion 600 has a base 620 and a lid 622. A medication, or some other fluid, enters the disposable portion 600 through the fluid inlet 606. The medication flows into the upstream fluid chamber 608 from the fluid inlet 606. Next, the medication flows through the flow restricting element 612 and into the downstream fluid chamber 614. The flow of the medication through the flow restricting element 612 results in a drop in fluid pressure as the fluid flows from the upstream fluid chamber 608 to the downstream fluid chamber 614 through the flow restricting element 612. Thus, during forward fluid flow under normal conditions, the fluid pressure within the upstream fluid chamber 608 is generally greater the fluid pressure within the downstream fluid chamber 614. The fluid pressure within the upstream fluid chamber 608 presses against a first area 611 of the fluid pressure membrane 610. Similarly, the fluid pressure within the downstream fluid chamber 614 presses against a second area 613 of the fluid pressure membrane 610.

The lid 622 forms an upstream opening 624 and a downstream opening 626 to allow the first and second areas 611, 613 of the fluid pressure membrane 610 to communicate, respectively, with the upstream pressure sensor 120 and the downstream pressure sensor 122 of the reusable portion 100. The first and second areas 611, 613 may be depressed slightly from the openings 624, 626 to better align the disposable portion for engagement with the sensors 120, 122.

The lid 622 is positioned such that the fluid pressure membrane 610 is positioned between the base 620 and the lid 622. The lid 622 and the base 620 are joined together to capture the fluid pressure membrane 610 between them. The lid 622 and the base 620 may be laser or ultrasonically welded together to form a fully assembled disposable portion 602, as viewed in FIG. 6.

The base 620 has a first recessed trough 628a located near a periphery of a top surface 630 of the base 620. The base 620 additionally has a second recessed trough 628b located near the top surface 629 on a wall 602 separating the upstream fluid chamber 608 from the downstream fluid chamber 614 transverse to the direction of fluid flow. The wall 602 is adjacent to, supports and seals against the flow restricting element 612 to separate the upstream and downstream fluid chambers 608, 614.

Figure 8:
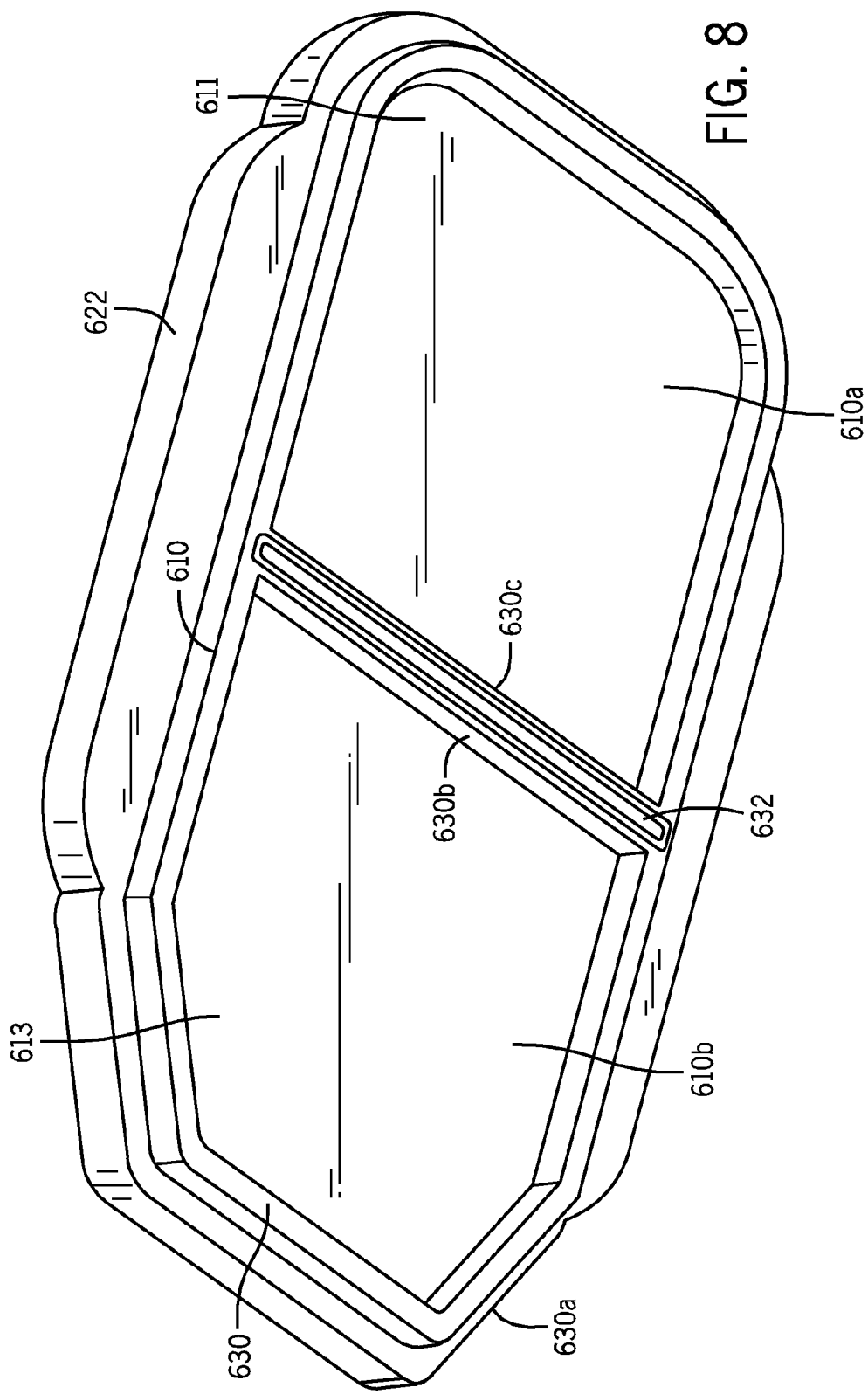
FIG. 8 is a pictorial view of a lid portion of the differential pressure based flow sensor assembly of FIG. 6.

As shown in FIG. 8, the lid 622 and the fluid pressure membrane 610 can be joined or injection molded in two shots or stages so that they form a single unit or integral piece. The fluid pressure membrane 610 comprises a first portion 610a and a second portion 610b. The first portion 610a is located upstream of the flow restricting element 612, and contains the first area 611 of the fluid pressure membrane 610. The membrane 610 has a first protruding lip 630a located near the periphery of the membrane 610. The second portion 610b is located downstream of the flow restricting element 612 and contains the second area 613 of the fluid pressure membrane 610. The first and second portions 610a, 610b of the fluid pressure membrane 610 have additional protruding lips 630b, 630c located adjacent to a transverse dividing member 632. In one embodiment, the protruding lips 630a, 630b and 620c are joined together at a central portion of the lid 622 and the dividing member 632 separates the first portion 610a and the second portion 610b of the fluid pressure membrane 610. As shown in FIG. 8, the dividing member 632 protrudes downwardly from the bottom surface of the lid 622. The dividing member 632 can be formed in the shape of a rectangular prism or can be a triangular or wedged prism with a wider base joined to the bottom surface of the lid 622 and a narrower tip at its distal end.

When the lid 622 is fitted to the base 620, the protruding lips 630a, 630b, 630c of the lid 622 enter the first and second recessed troughs 628a, 628b of the base 620. The inner periphery of the lips 630a, 630b, 630c are inclined so that the distal ends or tips of the lips are narrower than their base. This guides the lips 630a, 630b, 630c into the first and second recessed troughs 628a, 628b and stretches or puts the fluid pressure membrane 610 into tension to at least temporarily retain the lid 622 on the base 620. The protruding lips 630a, 630b, 630c form a fluid tight perimeter seal at the intersection of the lid 622 and the base 620. The dividing member 632 and a portion of each of the protruding lips 630b, 630c reside within the second recessed trough 628b when the lid 622 is applied to the base 620.

The lid 622 and the base 620 are secured or joined together to capture the fluid pressure membrane 610 between them. The lid 622 and the base 620 may be joined together using an ultrasonic welding or laser welding process. Advantageously, the dividing member 632 is also welded to the wall 602 and provides a more robust seal between the upstream and downstream fluid chambers 608, 614. It is further contemplated that an adhesive could be utilized to secure the lid 622 to the base 620.

It is contemplated that the flow restricting element 612 will be "insert" molded as an integral part of the base 620. In one embodiment, such as shown in FIGS. 6-9, the strip 615 that contains the flow restricting element 612 is placed within the base via an insert molding technique. For example, a continuous strip 615 of material may contain a plurality of flow restricting elements 612 located along the strip at a predefined distance. Each flow restricting element has an orifice 601 formed therethrough, as described above. The strip 615 may then be inserted into tooling, such as a mold, and the base 620 may be molded around a portion of the strip 615 containing a single flow restricting element 612 and orifice 601. Such a manufacturing process is efficient, low cost, and allows accurate control of the positioning of the flow restricting element 612 to help provide proper operational performance of the differential pressure based flow sensor assembly. Ensuring the proper placement of the flow restricting element 612 within the base 620 eases the assembly of the remainder of the remainder of the disposable portion 600 by not requiring a worker to position a flow restricting element 612 within a base 620 or a fluid pressure membrane 610.

As was also the case with the previously described embodiments, the flow restricting element 612 has an orifice 601 through it that provides fluid communication between the upstream fluid chamber 608 and the downstream fluid chamber 614 and thereby creates a fluid viscosity insensitive pressure drop when fluid flows therethrough. Several contemplated configurations and preferred dimensions of the orifice 601 are discussed in greater detail in the co-pending application U.S. Ser. No. 12/335,128, entitled Differential Pressure Based Flow Sensor Assembly For Medication Delivery Monitoring and Method of Using the Same and filed Dec. 15, 2008, which is incorporated by reference in its entirety herein. In the embodiment shown in FIG. 6-9, by virtue of the flatness of the strip 612, the upstream side of the flow restricting element 612 is substantially flat in a direction that is transverse or normal to the direction of fluid flow. However, on the downstream side of the flow restricting element 612, a funnel-shape or frusto-conical countersink 603 is formed in the side of the wall 602 adjacent to the downstream fluid chamber 614. The countersink 603 is registered, more particularly concentric, with the orifice 601. In one embodiment as shown, the countersink 603 has a centerline that is at least parallel with and more particularly coaxial with the central longitudinal axis of the orifice 601. The countersink 603 defines an inner surface that is angled or inclined with respect to the horizontal centerline of the countersink 603. The surface is inclined at an angle of about 45-60 degrees from the horizontal centerline of the countersink 603, more particularly about 45-50 degrees, and most particularly about 45 degrees. The countersink 603 allows the effective length of the orifice in the flow direction to be controlled to a short length by virtue of the thickness of the strip 612. The countersink 603 and the wall 602 provide good mechanical support for the strip 612 and its orifice 601 while keeping the effective length of the orifice 601 as short as possible so the flow sensor assembly is relatively insensitive to the viscosity of the fluid whose flow characteristics are being determined. The strip 612 is about 0.0001-0.0008 inch thick, more particularly about 0.0001-0.0005 inch thick, and most particularly about 0.0005 inch thick, especially in the vicinity of the orifice 601.

As shown in FIGS. 6-9, the fluid pressure membrane 610 is a flexible diaphragm type membrane. The fluid pressure membrane 610 may be formed from silicone, or some other flexible polymeric material or elastomeric material. The fluid pressure membranes 610 may comprise a variety of polymeric or elastomeric materials, such as TPE, or silicone.

It is contemplated that a variety of materials may be utilized for the manufacture of the disposable portion 600. The disposable portion 600 may comprise a thermoplastic. It is contemplated that the flow restricting element 612 may comprise a different material than the rest of the base 620. Non-limiting examples of the material that may be utilized to form the flow restricting element 612 include a stainless steel or other metal, medical grade thermoplastics and elastomers. The orifice 601 in the flow restricting element 612 can be formed by molding, laser microdrilling, chemical etching, die cutting or stamping.

Figure 9:
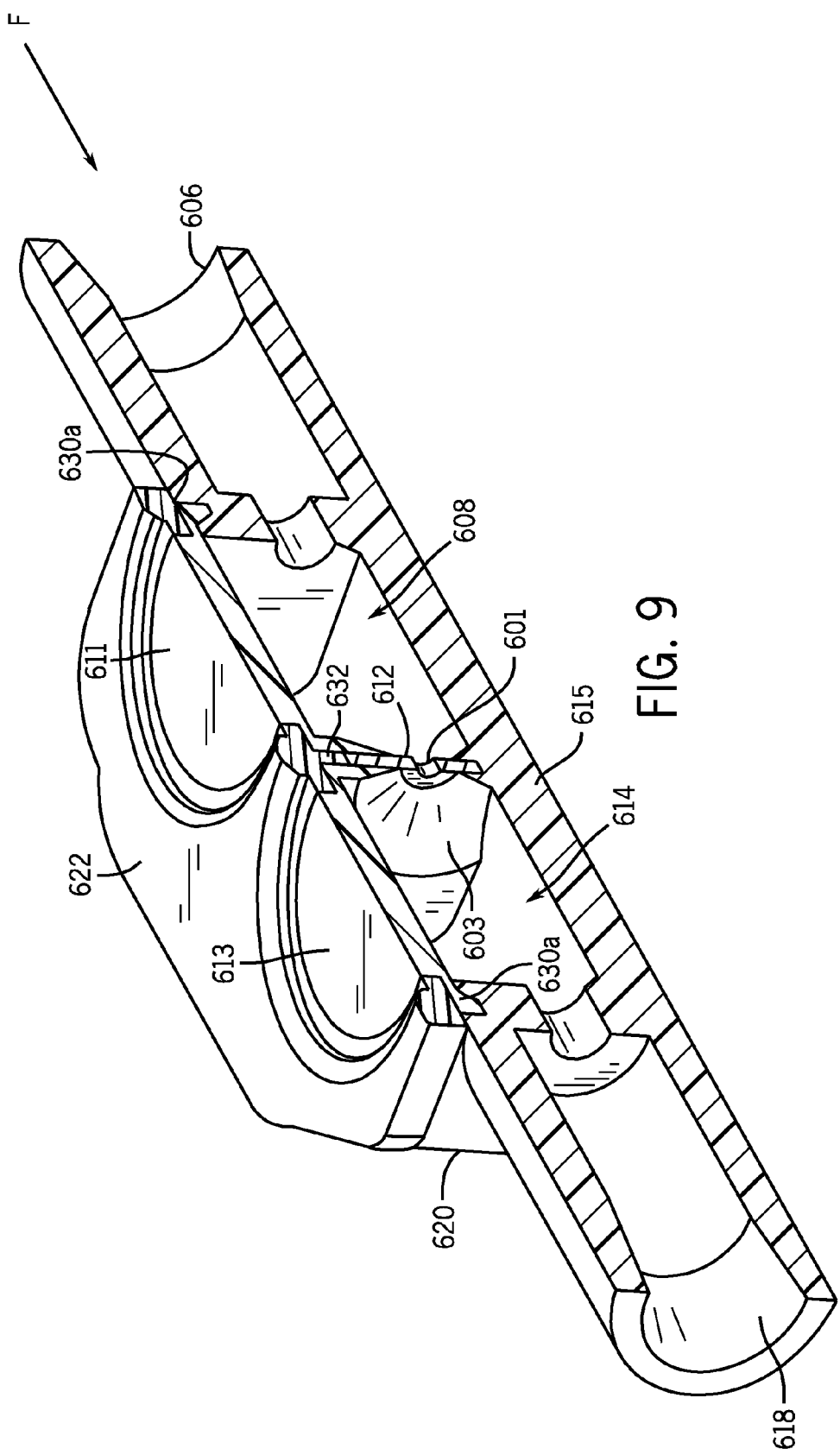
FIG. 9 is a cross sectional view of the disposable portion of the differential pressure based flow sensor assembly of FIG. 6 taken along line 9-9 of FIG. 6.

As shown in FIG. 9, medication enters the disposable portion 600 through the fluid inlet 606. The medication flows into the upstream fluid chamber 608 from the fluid inlet 606. Next, the medication flows through the flow restricting element 612 and into the downstream fluid chamber 614. The flow of the medication through the flow restricting element 612 results in a drop in fluid pressure as the fluid flows from the upstream fluid chamber 608 to the downstream fluid chamber 614 through the flow restricting element 612. Thus, during forward fluid flow under normal conditions, the fluid pressure within the upstream fluid chamber 608 is generally greater the fluid pressure within the downstream fluid chamber 614. The fluid pressure within the upstream fluid chamber 608 presses against the first area 611 fluid pressure membrane 610, causing the first area 611 of the membrane 610 to be displaced upward in the upstream opening 624 of the lid 622 to press against an upstream fluid pressure sensor (See FIG. 3, 120). Similarly, the fluid pressure within the downstream fluid chamber 614 presses against the second area 613 of the fluid pressure membrane 610, causing the second area 613 of the membrane 610 to be displaced upward in the downstream opening 626 of the lid 622 to press against a downstream fluid pressure sensor (See FIG. 3, 122).

Turning now to FIGS. 10-16 a disposable portion 1000 is shown according to a further embodiment. The disposable portion 1000 comprises: a fluid inlet 1006; an upstream fluid chamber 1008; a fluid pressure membrane 1010; a flow restricting element 1012; a downstream fluid chamber 1014; and a fluid outlet 1018. The membrane 1010 is fluid impermeable. The disposable portion 1000 has a base 1020 and a lid 1022. A medication, or some other fluid, enters the disposable portion 1000 through the fluid inlet 1006. The medication flows into the upstream fluid chamber 1008 from the fluid inlet 1006. Next, the medication flows through the flow restricting element 1012 and into the downstream fluid chamber 1014. The flow of the medication through the flow restricting element 1012 results in a drop in fluid pressure as the fluid flows from the upstream fluid chamber 1008 to the downstream fluid chamber 1014 through the flow restricting element 1012. Thus, during forward fluid flow under normal conditions, the fluid pressure within the upstream fluid chamber 1008 is generally greater the fluid pressure within the downstream fluid chamber 1014. The fluid pressure within the upstream fluid chamber 1008 presses against a first area 1011 of the fluid pressure membrane 1010. Similarly, the fluid pressure within the downstream fluid chamber 1014 presses against a second area 1013 of the fluid pressure membrane 1010.

The lid 1022 forms an upstream opening 1024 and a downstream opening 1026 to allow the first and second areas 1011, 1013 of the fluid pressure membrane 1010 to communicate, respectively, with the upstream pressure sensor 120 and the downstream pressure sensor 122 of the reusable portion 100. The first and second areas 1211, 1213 may be depressed slightly from the openings 1224, 1226 to better align the disposable portion for engagement with the sensors 120, 122.

The lid 1022 is positioned such that the fluid pressure membrane 1010 is positioned between the base 1020 and the lid 1022. The lid 1022 and the base 1020 are joined together to capture the fluid pressure membrane 1010 between them. The lid 1022 and the base 1020 may be laser or ultrasonically welded together to form a fully assembled disposable portion 1002, as viewed in FIG. 13.

Figure 11:
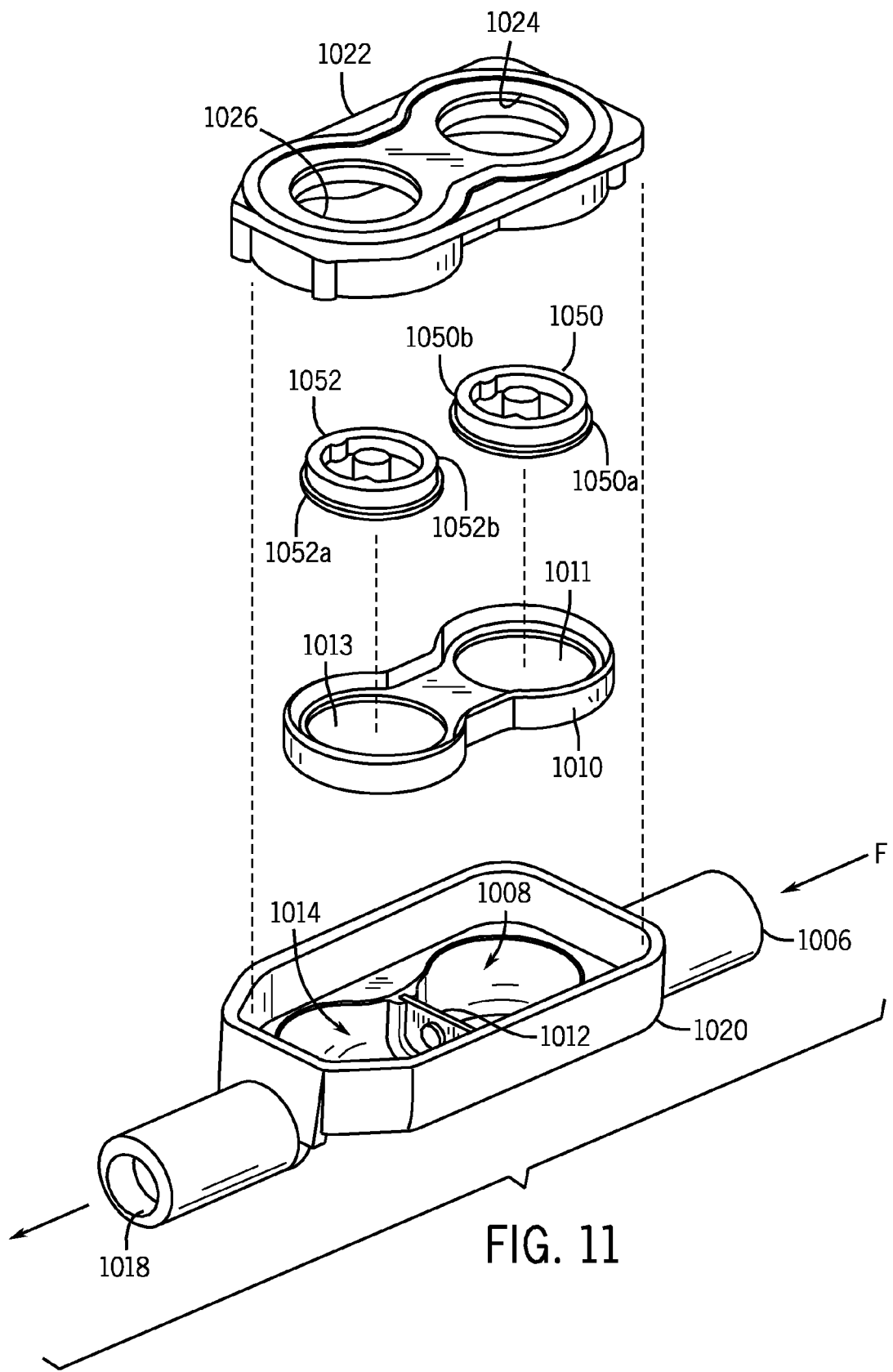
FIG. 11 is an exploded view of the disposable portion of the differential pressure based flow sensor assembly of FIG. 10.
Figure 15:
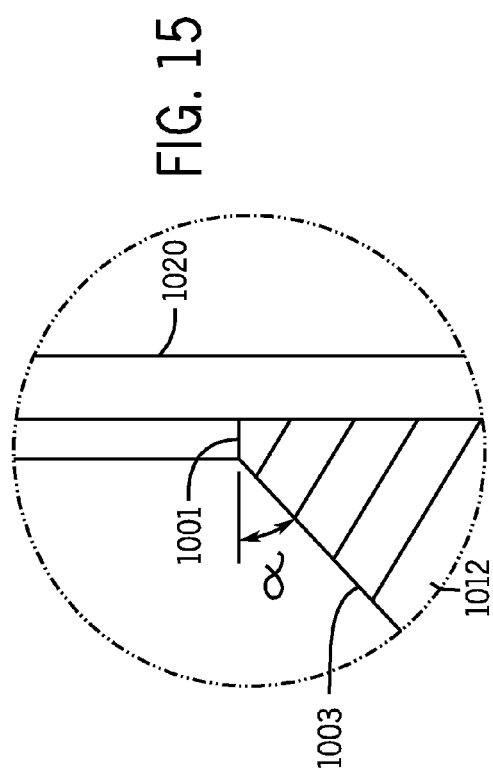
FIG. 15 is an enlarged cross sectional view of the orifice of the flow restricting element of the embodiment of FIG. 10.
Figure 12:
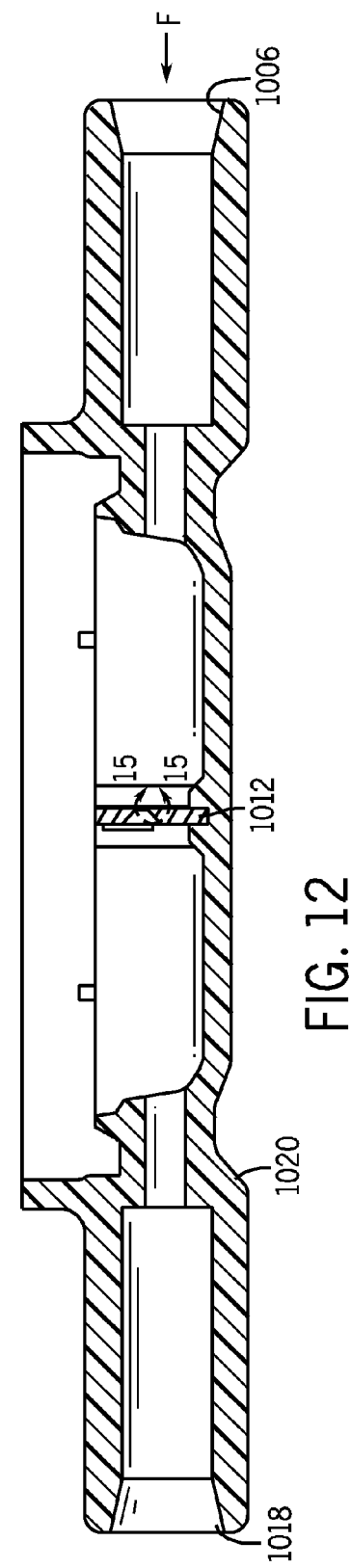
FIG. 12 is a central longitudinal cross sectional view of a base or body assembly portion of the differential pressure based flow sensor assembly of FIG. 10.
Figure 13:
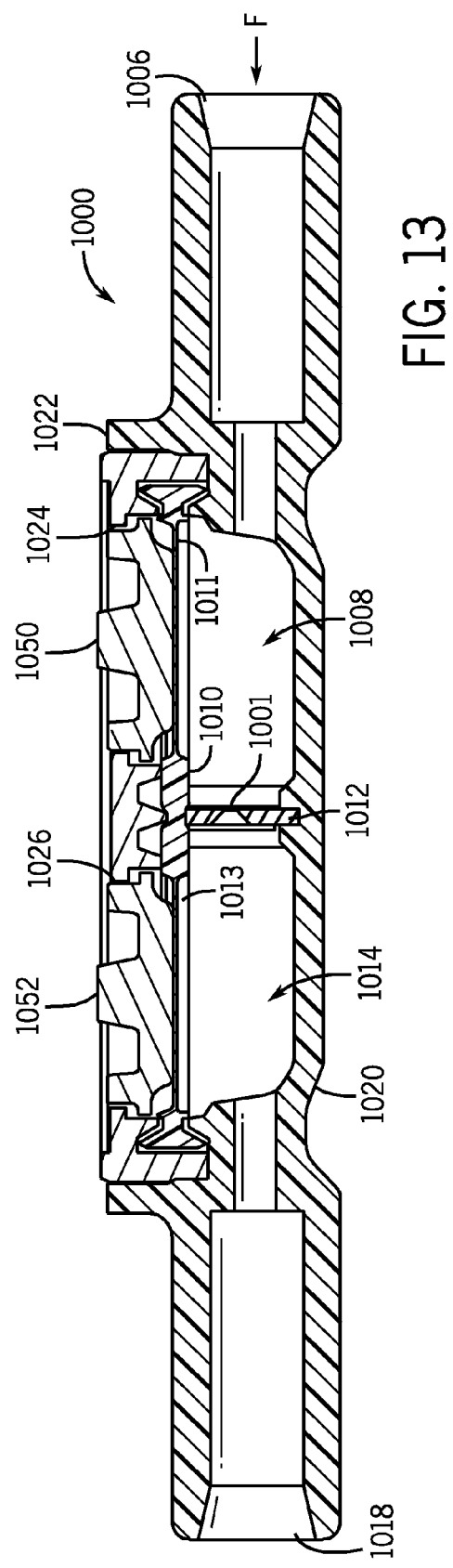
FIG. 13 is a cross sectional view of the differential pressure based flow sensor assembly of FIG. 10 taken along line 13-13 of FIG. 10.

As best shown in FIGS. 11 and 13, the disposable portion 1000 further comprises a first rigid disk 1050 and a second rigid disk 1052 positioned above the first area 1011 and the second area 1013 of the membrane 1010 between the membrane 1010 and the lid 1022. Thus, as pressure is applied to the membrane 1010 by the flow of fluid, the first and second areas 101 1, 1013 of the membrane 1010 are pushed upward towards the openings 1024, 1026 of the lid 1022, thus moving the rigid disks 1050, 1052 towards the openings 1024, 1026. The rigid disks 1050, 1052 contact the lid 1022 as the membrane 1010 is raised by the pressure of the fluid flow. Once the rigid disks 1050, 1052 contact the lid 1022 the first and second areas 1011, 1013 of the membrane 1010 are constrained and may not continue to move towards the lid 1022. Thus, the rigid disks 1050, 1052 prevent the membrane 1010 from being displaced to an extent that the membrane 1010 is likely to fail.

The use of the rigid disks 1050, 1052 allows the disposable portion 1000 to withstand higher operating pressures, without requiring the thickness of the membrane 1010 in the first and second areas 1011, 1013 to become so thick that sensitivity of the sensor assembly 10 is degraded.

The rigid disk 1050 has a ledge portion 1050*a* that is adapted to contact the lid 1022, and a protruding portion 1050*b* that is adapted to interact with a sensor 120 within the reusable portion 100. Thus, as fluid flows through the disposable portion 1000, the first area 1011 of the membrane 1010 is displaced toward the lid 1022, causing the protruding portion 1050*b* of the rigid disk 1050 to pass through the opening 1024 of the lid 1022. However, once the pressure within the upstream chamber 1008 reaches a certain level, the ledge portion 1050*a* of the rigid disk 1050 contacts the lid 1022, preventing further displacement of the first area 1011 of the membrane 1010.

Similarly, the second rigid disk 1052 has a ledge portion 1052*a* that is adapted to contact the lid 1022, and a protruding portion 1052*b* that is adapted to interact with a sensor 122 within the reusable portion 100. Thus, as fluid flows through the disposable portion 1000, the second area 1013 of the membrane 1010 is displaced toward the lid 1022, causing the protruding portion 1052*b* of the rigid disk 1050 to pass through the opening 1026 of the lid 1022. However, once the pressure within the downstream chamber 1010 reaches a certain level, the ledge portion 1052*a* of the rigid disk 1052 contacts the lid 1022, preventing further displacement of the second area 1013 of the membrane 1010.

Therefore, the membrane 1010 may be subjected to much higher pressure before failing based on the rigid disks 1050, 1052 limiting the displacement of the membrane 1010.

It is contemplated that the flow restricting element 1012 will be placed within the base 1020 via an insert molding technique. For example, a flow restricting element 1012 is placed within tooling, such as a mold, and the base 1020 is molded around the flow restricting element. Such a manufacturing process is low cost, efficient and allows accurate control of the positioning of the flow restricting element 1012 to help provide proper operational performance of the differential pressure based flow sensor assembly. Further, manufacturing of the disposable assembly 1000 is simplified as a worker does not have to align the flow restricting element 1012 within the flow path, as the flow restricting element is already formed within the base 1020. Of course, in another embodiment, the base 1020 can be formed or molded separately and a slot can be provided in the base 1020 and/or the membrane 1010 for receiving the flow restricting element 1012. An adhesive or means of securing the element 1012 in place and sealing between the fluid chambers 1008 and 1014 would be used in that embodiment.

Figure 10:
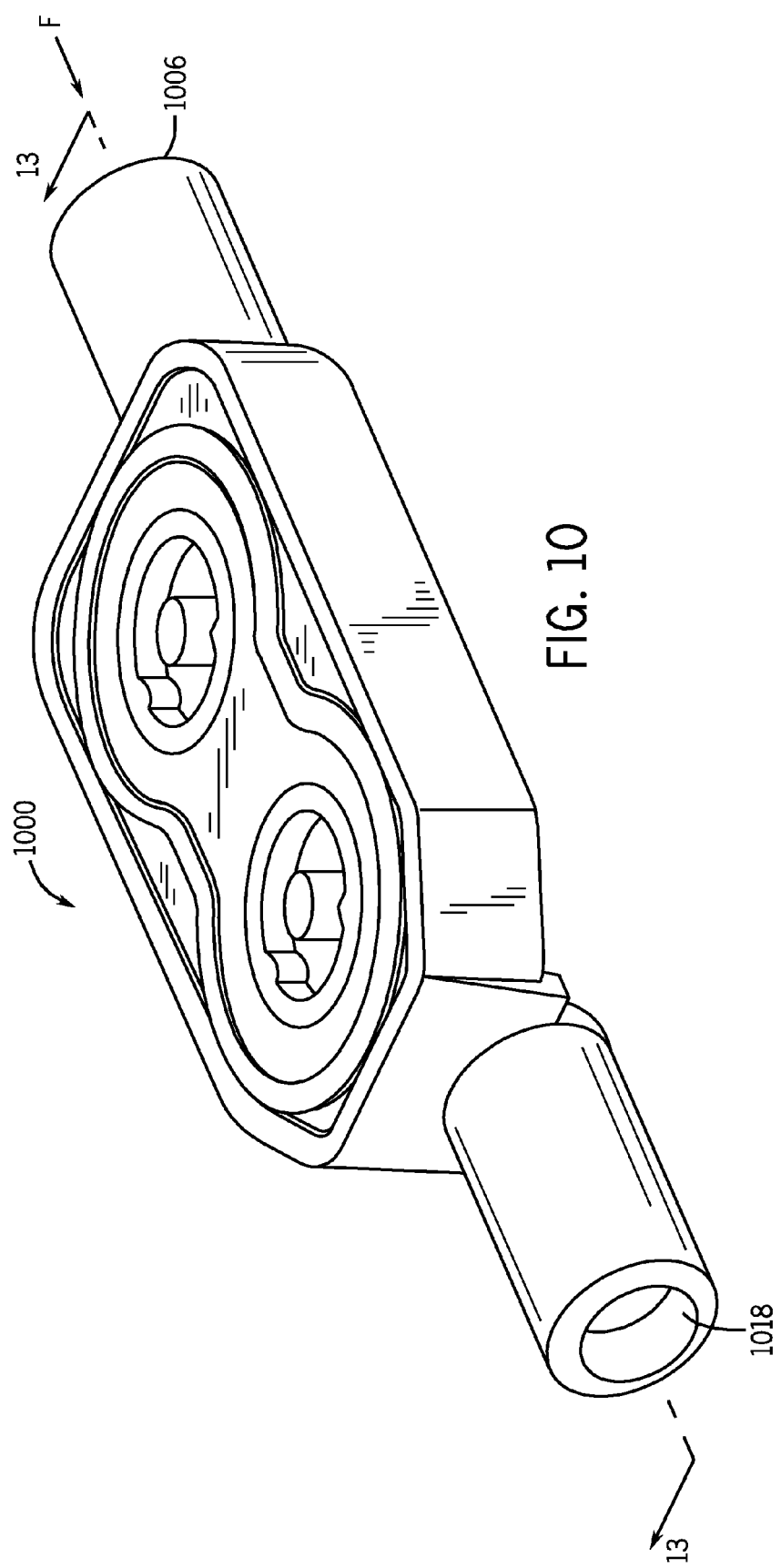
FIG. 10 is a pictorial view of a disposable portion of a differential pressure based flow sensor assembly according to yet another embodiment.

As shown in FIG. 10, medication enters the disposable portion 1000 through the fluid inlet 1006. The medication flows into the upstream fluid chamber 1008 from the fluid inlet 1006. Next, the medication flows through the flow restricting element 1012 and into the downstream fluid chamber 1014. The flow of the medication through the flow restricting element 1012 results in a drop in fluid pressure as the fluid flows from the upstream fluid chamber 1008 to the downstream fluid chamber 1014 through the flow restricting element 1012. Thus, during forward fluid flow under normal conditions, the fluid pressure within the upstream fluid chamber 1008 is generally greater the fluid pressure within the downstream fluid chamber 1014. The fluid pressure within the upstream fluid chamber 1008 presses against the first area 1011 fluid pressure membrane 1010, causing the first area 1011 of the membrane 1010 to be displaced upward in the upstream opening 1024 of the lid 1022 to press against an upstream fluid pressure sensor (See FIG. 3, 120). Similarly, the fluid pressure within the downstream fluid chamber 1014 presses against the second area 1013 of the fluid pressure membrane 1010, causing the second area 1013 of the membrane 1010 to be displaced upward in the downstream opening 1026 of the lid 1022 to press against a downstream fluid pressure sensor (See FIG. 3, 122).

As best seen in FIGS. 11-16 the flow restricting element 1012 is formed by micromolding, machining, etching or a combination thereof. The orifice 1001 in the flow restricting element 1012 can be formed by molding, laser microdrilling, chemical etching, die cutting or stamping. When the flow restricting element 1012 is formed as a wafer by micromolding, the whole base assembly can be formed in a two shot or two stage molding process. As was the case in the embodiment shown in FIG. 6-9, the upstream side of the flow restricting element 1012 is substantially flat in a direction that is transverse or normal to the direction of fluid flow. However, on the downstream side of the flow restricting element 1012, a funnel-shape or frusto-conical countersink 1003 is formed in the side of the wall 1002 adjacent to the downstream fluid chamber 1014. The countersink 1003 is registered, more particularly concentric, with the orifice 1001. In one embodiment as shown, the countersink 1003 has a centerline that is at least parallel with and more particularly coaxial with the central longitudinal axis of the orifice 1001. The countersink 1003 defines an inner surface that is angled or inclined with respect to the horizontal centerline of the countersink 1003. The surface is inclined at an angle $\alpha$ of about 45-60 degrees from the horizontal centerline of the countersink 1003, more particularly about 45-50 degrees, and most particularly about 45 degrees. The countersink 1003 allows the effective length of the orifice in the flow direction to be controlled to a short length by virtue of the thickness of the surrounding or immediately adjacent area of the flow restricting element 1012. The countersink 1003 leaves good mechanical support for the orifice 1001 while keeping the effective length of the orifice 1001 as short as possible so the flow sensor assembly is relatively insensitive to the viscosity of the fluid whose flow characteristics are being determined. The effective length of the orifice 1001 of the flow restricting element 1012 is about 0.0001-0.0008 inch, more particularly about 0.0001-0.0005 inch, and most particularly about 0.0005 inch.

Figure 14:
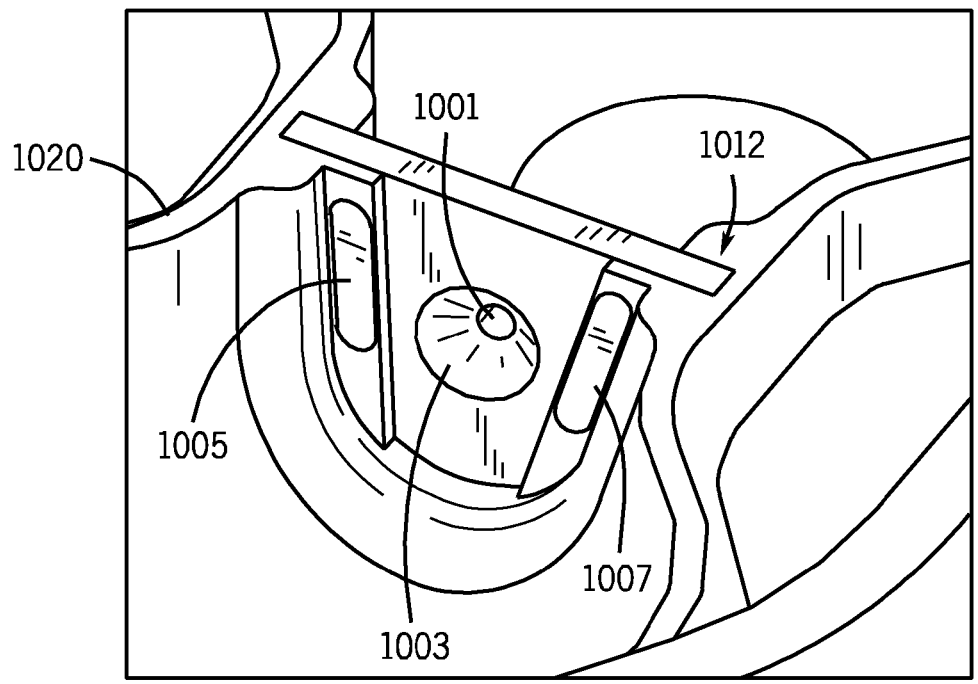
FIG. 14 is an enlarged pictorial view of the area surrounding the flow restricting element in the body assembly of FIG. 10.
Figure 16:
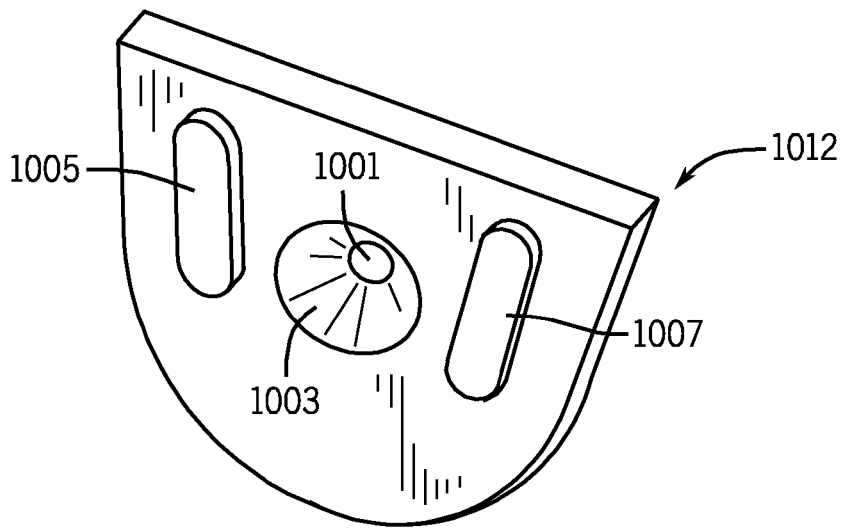
FIG. 16 is an enlarged pictorial view of the flow restricting element insert from FIG. 12.

As best seen in FIG. 16, the flow restricting element 1012 is formed with a planar upper edge and a U-shaped lower side edge. As shown in FIGS. 13 and 14, the planar upper edge of the flow restricting element can be positioned so as to be at least flush or raised above the membrane engaging surface of the base 1020. Thus, the lid 1022 and the base assembly squeeze the membrane 1010 for improved sealing. On the downstream or countersunk side of the element 1012 a pair of detents 1005, 1007 are formed on opposite sides of the orifice 1001 to aid in securing the molded body to the flow restricting element 1012. The detents 1005, 1007 can be indentations or can be raised as shown to aid in locating or positioning the components relative to each other during manufacture. When the detents 1005, 1007 are raised, they may also serve as an inlet and outlet for material in the molding process.

As seen in FIGS. 11 and 14, the base 1020 has a raised figure eight shaped peripheral sealing rim that is generally aligned or registered with an opposing rim that extends downwardly from the lid 1022. The membrane 1010 is captured and compressed between these rims to form a fluid tight seal.

While the foregoing has described what are considered to be the best mode and/or other examples, it is understood that various modifications may be made and that the subject matter disclosed herein may be implemented in various forms and examples, and that they may be applied in numerous other applications, combinations and environments, only some of which have been described herein. Those of ordinary skill in that art will recognize that the disclosed aspects may be altered or amended without departing from the true scope of the subject matter. Therefore, the subject matter is not limited to the specific details, exhibits and illustrated examples in this description. It is intended to protect any and all modifications and variations that fall within the true scope of the advantageous concepts disclosed herein.

We claim:

1. A disposable assembly for releasable coupling engagement with a reusable flow sensor assembly, the disposable assembly comprising:
   a body having a lid portion and a base portion, the body defining a fluid flow passage and forming an inlet and an outlet, the lid portion having a first opening and a second opening and being secured to the base portion;
   a flow restricting element extending completely across the fluid flow passage at a location between the inlet and the outlet and between the first opening and the second opening, the flow restricting element having an orifice formed therethrough and being positioned in the base portion;
   a fluid pressure membrane disposed along the fluid flow passage between the inlet and the outlet, the fluid pressure membrane being captured between the lid portion and the base portion of the body and defining a fluid pressure responsive movable wall having an external surface remote from the fluid flow passage, the external surface being accessible through the first opening and the second opening of the lid portion for releasable coupling engagement with the reusable flow sensor assembly.

2. The disposable assembly of claim 1, wherein the fluid pressure membrane has a first area and a second area adapted to be aligned respectively with the first opening and the second opening of the lid portion.

3. The disposable assembly of claim 1, wherein the flow restricting element is integrally molded into an upright wall of the base portion.

4. The disposable assembly of claim 1, wherein the flow restricting element comprises a strip of material having an orifice and the strip of material is provided as a separate component that is subsequently molded into the base portion.

5. The disposable assembly of claim 2, the fluid pressure membrane first area is a first membrane portion and the fluid pressure membrane second area is a second membrane portion, the first membrane portion and the second membrane portion being separate membranes.

6. The disposable assembly of claim 5, wherein first membrane portion has a first protruding lip and the second membrane portion has a second protruding lip, the first protruding lip and the second protruding lip being adapted to interact with a trough in the base portion to form a fluid tight seal between the lid portion and the base portion.

7. The disposable assembly for use with a flow sensor assembly of claim 6, wherein the base portion and the lid portion of the body are ultrasonically welded together.

8. The disposable assembly of claim 1, wherein the flow restricting element comprises a micromolded orifice chip that is subsequently molded into the base portion to complete a two-shot molding process.

9. The disposable assembly of claim 8, wherein the flow restricting element and the base portion comprise the same material.

10. A method of forming a disposable portion for releasable coupling engagement with a reusable fluid flow sensor assembly comprising:
    providing a preformed flow restricting element having an orifice formed therethrough;
    forming a base portion around the flow restricting element using a mold and an injection molding process, the base portion forming at least a portion of a fluid flow passage having an inlet and an outlet, the inlet being in fluid communication with an upstream side of the flow restricting element and the outlet being in fluid communication with a downstream side of the flow restricting element;

positioning a fluid pressure membrane along the fluid flow passage between the inlet and the outlet, the fluid pressure membrane contacting the base portion and defining a fluid pressure responsive movable wall having an external surface remote from the fluid flow passage; and securing a lid portion to the base portion, the lid portion having a first opening on the upstream side of the flow restricting element and a second opening on the downstream side of the flow restricting element, the fluid pressure membrane being positioned between the lid portion and the base portion following the securing step such that the external surface is accessible through the first opening and the second opening for releasable coupling engagement with the reusable fluid flow sensor assembly.

11. The method of claim 10, wherein the act of providing the flow restricting element includes supplying a strip of material having a plurality of orifices located at predetermined intervals and positioning a single orifice within the mold used in the forming of the base portion.

12. The method of claim 10, wherein the act of providing the preformed flow restricting element includes supplying a single molded flow restricting element having an orifice and positioning the preformed flow restricting element within a mold used in forming the base portion.

13. The method of claim 10, wherein the securing the lid portion to the base portion includes ultrasonic welding.

14. The disposable assembly of claim 1, wherein the base portion includes a loop-shaped peripheral sealing element formed thereon.

15. The disposable assembly of claim 1, wherein the lid portion includes an opposing loop-shaped peripheral sealing element formed thereon that mates with the loop-shaped peripheral sealing element on the base portion when the lid portion is secured to the base portion.

* * * * *